(12) United States Patent
Schönlein et al.

(10) Patent No.: US 7,368,730 B2
(45) Date of Patent: May 6, 2008

(54) WEATHERING APPARATUS WITH UV RADIATION SOURCES AND RADIATION SENSORS CONTAINING A DOUBLE-CALIBRATED UV SENSOR

(75) Inventors: Artur Schönlein, Rüsselsheim (DE); Peter March, Frankfurt (DE)

(73) Assignee: Atlas Material Testing Technology GmbH (DE)

( * ) Notice: Subject to any disclaimer, the term of this patent is extended or adjusted under 35 U.S.C. 154(b) by 183 days.

(21) Appl. No.: 11/195,847

(22) Filed: Aug. 3, 2005

(65) Prior Publication Data
US 2006/0027761 A1 Feb. 9, 2006

(30) Foreign Application Priority Data
Aug. 3, 2004 (DE) ............ 10 2004 037 602

(51) Int. Cl.
*A61N 5/00* (2006.01)
(52) U.S. Cl. .......... 250/492.1; 250/372; 250/504 R; 250/493.1; 250/494.1; 356/51
(58) Field of Classification Search ......... 250/372, 250/504 R, 493.1, 494.1; 356/51
See application file for complete search history.

(56) References Cited

U.S. PATENT DOCUMENTS

| 3,686,940 | A | * | 8/1972 | Kockott ............... 73/150 R |
| 4,391,522 | A |   | 7/1983 | Schmid et al. |
| 4,644,166 | A | * | 2/1987 | Sturm et al. ............ 250/372 |
| 4,807,247 | A | * | 2/1989 | Robbins, III ............ 374/57 |
| 5,206,518 | A | * | 4/1993 | Fedor et al. ........... 250/504 R |
| 5,220,840 | A |   | 6/1993 | Neigoff et al. |
| 5,898,816 | A | * | 4/1999 | Heeger et al. .......... 392/408 |
| 6,525,493 | B2 | * | 2/2003 | Grossman et al. ....... 315/291 |
| 7,038,196 | B2 | * | 5/2006 | Scott et al. .......... 250/252.1 |
| 2005/0018744 | A1 | * | 1/2005 | Schonlein et al. ....... 374/2 |
| 2005/0167580 | A1 | * | 8/2005 | Scott et al. .......... 250/252.1 |
| 2006/0027761 | A1 | * | 2/2006 | Schonlein et al. ....... 250/372 |

FOREIGN PATENT DOCUMENTS

| DE | 2043217 | 3/1971 |
| DE | 2940325 A1 | 4/1981 |
| DE | 3310631 C2 | 10/1984 |
| DE | 195 09 576 C1 | 3/1995 |
| EP | 1248097 | 10/2002 |
| FR | 2059300 | 5/1971 |

OTHER PUBLICATIONS

European Patent Office, Automated English translation of French Patent No. 2,059,300.

* cited by examiner

*Primary Examiner*—David Porta
*Assistant Examiner*—Casey Bryant
(74) *Attorney, Agent, or Firm*—Vedder Price P.C.

(57) ABSTRACT

Weathering apparatus with UV radiation sources and radiation sensors containing a double-calibrated UV sensor A weathering apparatus has one or more UV radiation sources (2) and one or more first sensors (3), which are calibrated for a first spectral sensitivity range. In a first aspect of the invention, the sensor or one of the first sensors (3) is calibrated in such a way that the radiation power of a spectral range which is located within the first spectral sensitivity range can be determined from its output signal. In a second aspect of the invention, a second sensor (4) is provided, which is calibrated for a second spectral sensitivity range.

18 Claims, 1 Drawing Sheet

IS: 300-400nm
NB1: 340±10nm
NB2: 420±10nm

WEATHERING APPARATUS WITH UV RADIATION SOURCES AND RADIATION SENSORS CONTAINING A DOUBLE-CALIBRATED UV SENSOR

FIELD OF THE INVENTION

Weathering apparatus with UV radiation sources and radiation sensors containing a double-calibrated UV sensor. The present invention relates to a weathering apparatus according to the precharacterizing clause of Patent claim 1.

BACKGROUND OF THE INVENTION

In a weathering apparatus, the weather-dependent aging behaviour of a sample, in particular of a flat material sample, is assessed, with the sample being subjected to artificial weathering. The weathering apparatus for this purpose normally has a weathering chamber, in which holding means are arranged for holding samples to be weathered, and in which one or more radiation sources are arranged in order to apply radiation, in particular UV radiation, to the samples.

Apparatuses for artificial weathering of material samples are generally used to estimate the life of materials which are continuously subjected to natural weather conditions during their use, and which thus deteriorate under climatic influences such as sunlight, solar heat, humidity and the like. In order to obtain a good simulation of the natural weathering characteristics, it is advantageous for the spectral energy distribution of the light produced in the apparatus to correspond as far as possible to that of the natural solar radiation, for which reason appliances such as these use xenon emitters as their radiation source. In addition, an accelerated ageing test of the materials is achieved essentially by illuminating the samples more intensively than the natural conditions, thus speeding up the ageing of the samples. A statement about the long-term ageing behaviour of a material sample can thus be made after a relatively short time.

The majority of the material samples which are investigated in artificial weathering appliances are composed of polymer materials. The weather-dependent deterioration of polymer materials is caused substantially by the UV component of the solar radiation. The primary photochemical processes which take place in this case, that is to say the absorption of photons and the production of stimulated states or free radicals, are not dependent on the temperature. In contrast, the subsequent reaction steps with the polymers or additives may be dependent on the temperature, so that the observed ageing of the materials is likewise dependent on the temperature.

One or more UV radiation sources, such as xenon radiation sources, is or are optionally used in the previously known weathering apparatuses. As is known, these allow the entire solar spectrum to be simulated quite well, in which case the relatively high spectral component in the infrared spectral range can be attenuated by suitable IR filters.

The radiation power emitted from the UV radiation sources is measured by UV sensors, in which case it is possible to provide for each UV radiation source to have its own associated UV sensor. The output signal from the UV sensors is supplied to a control and recording device in which the UV radiation powers can be recorded during a weathering process. Furthermore, the output signals from the UV sensors can be supplied to a control device, by means of which the electrical power to be supplied to the power supply devices for the UV radiation sources can be regulated at constant UV radiation power levels.

It is known for broadband UV sensors to be used in weathering apparatuses, which have a sensitivity range in the range from 300 nm to 400 nm, in accordance with the IS Standard. However, there is also frequently a requirement for weathering processes to be carried out with the UV radiation power being measured using the NB Standard. In this Standard, the radiation power is optionally measured in the two narrowband ranges of 340 nm ±10 nm or 420±10 nm, with the latter range being outside the UV range, in the visible, blue spectral range. However, in the prior art, there are only sensors which are calibrated for in each case one of the already mentioned three sensitivity ranges. Accordingly, if there is a wish to use a different standard for the radiation power measurement from one weathering process to the next, in particular based on a different sensitivity range, then it is either necessary to replace the sensors or, if this is not possible, a different weathering apparatus must be used.

A change in the Standard for the measurement of the radiation power is accordingly associated with considerable effort and additional costs in the prior art.

SUMMARY OF THE INVENTION

One object of the present invention is accordingly to specify a weathering apparatus which allows weathering processes to be carried out using different power measurement standards, with relatively little effort.

This object is achieved by the characterizing features of Patent claim 1. This object is likewise achieved by the characterizing features of the other independent Patent claim 2. Advantageous developments and refinements are the subject matter of dependent claims.

A weathering apparatus in accordance with the present invention has one or more UV radiation sources and one or more first sensors, which are calibrated for a first spectral sensitivity range in the UV and each produce an output signal which is representative of the radiation power received in the first sensitivity range. The first sensitivity range may be a broadband range from 300 nm to 400 nm.

One major idea according to a first aspect of the present invention relates to the first sensor or one of the first sensors additionally being calibrated in such a way that the radiation power of a spectral range which is located within the first sensitivity range can be determined from its output signal.

This spectral range may in this case extend from 330 nm to 350 nm, and thus corresponds to the measurement range of 340 nm 110 nm, as specified in the NB Standard.

One major idea according to a second aspect of the present invention relates to a second sensor being provided in addition to the first sensor or sensors, and being calibrated for a second spectral sensitivity range.

This second spectral sensitivity range may extend from 410 nm to 430 nm, and thus corresponds to the measurement range of 420 nm ±10 nm, as likewise specified in the NB Standard. This range is outside the UV, in the visible blue spectral range. A measurement in this range thus makes use of the fact that certain UV radiation sources also emit in the adjacent visible spectral range, and the radiation power in this measurement range has a constant ratio to the radiation power in the UV range.

The two aspects of the present invention can be combined with one another in a particularly advantageous manner, thus making it possible to record all three spectral ranges, as mentioned further above, for measurement purposes in one weathering process using a small number of sensors in one weathering apparatus.

This becomes more significant, the greater the number of UV radiation sources in the weathering apparatus.

One advantageous refinement of the invention is for the weathering apparatus to have a number of UV radiation sources, one of which is in each case associated with one of the first sensors and detects essentially only the UV radiation from the respectively associated UV radiation source. By way of example, the weathering apparatus may have two, three or even more than three UV radiation sources and may have a corresponding number of first sensors, which are each arranged in such a way that they detect only the radiation from the respectively associated radiation source.

In the case of three UV radiation sources in the weathering apparatus, it is sufficient—as will be seen later—to use four sensors in order to record the three sensitivity ranges (as mentioned further above) for measurement purposes, while a total of nine sensors would be necessary for this purpose in conventional appliances.

However, according to the invention, it is also possible to provide for the weathering apparatus to have only a single UV radiation source. It is then possible to arrange one and only one first sensor in the weathering apparatus, and to additionally calibrate this first sensor for the spectral range within the first sensitivity range. Additionally or as an alternative to this, a second sensor can then be provided so that a total of two sensors would be provided in a case such as this.

In the second aspect of the present invention, the second sensor is preferably associated with one specific UV radiation source (reference radiation source) of a number of UV radiation sources, and it detects essentially only the radiation emitted by this associated UV radiation source in the second sensitivity range. This second sensor can then also be used to derive the radiation powers from the other UV radiation sources in the second spectral sensitivity range from the output signal from its associated first sensor and the output signals from the first and the second sensor for the reference radiation source.

According to a further advantageous embodiment, the weathering apparatus according to the invention has a weathering chamber in which the UV radiation sources and the sensors are accommodated, wherein the UV radiation sources are arranged along a first wall of the weathering chamber, and the samples to be weathered are arranged along a second wall, which is opposite the first wall, and the sensors are fitted to a third wall, which connects the first wall and the second wall, and in particular are inserted into openings in the third wall.

In this case, the sensors are preferably used in such a way that they are aligned at an inclined angle to the respective UV radiation sources associated with them.

One exemplary embodiment of the present invention will be explained in more detail in the following text with reference to the drawing figures, in which:

DETAILED DESCRIPTION OF THE INVENTION

Figure 1:
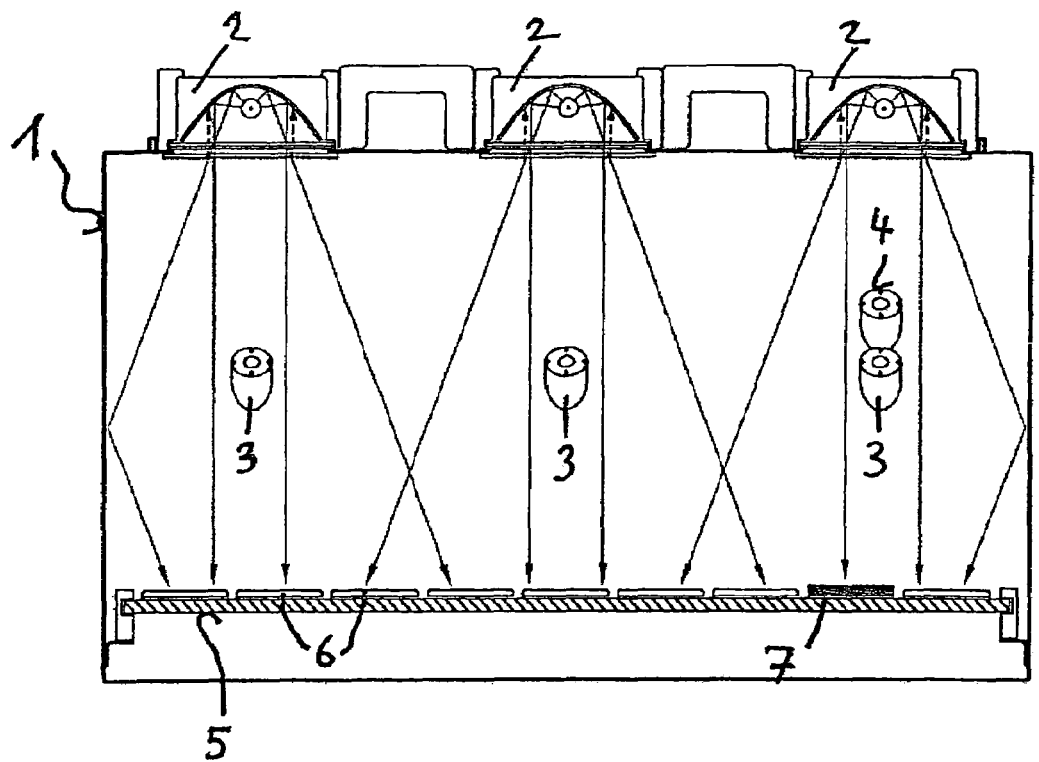
FIG. 1 shows one embodiment of a weathering apparatus according to the invention.

FIG. 1 shows a longitudinal section through a weathering chamber 1 in a weathering apparatus. Openings in which UV radiation sources 2 are inserted are provided in one longitudinal wall of the weathering chamber 1. In the present case, the UV radiation sources 2 are formed by xenon radiation sources. The discharge tubes, which are filled with xenon, are surrounded by metallic reflectors in a known manner in each radiation source 2, so that virtually all of the radiation emitted from the radiation source 2 enters the interior of the weathering chamber 1. Infrared filters may be placed in front of the radiation sources 2 to remove the relatively high infrared component from the spectrum emitted by xenon lamps. The inner walls of the weathering chamber 1 are advantageously coated with aluminum in order to increase the degree of reflection in the UV range and thus likewise to use the UV radiation reflected on the inner walls for application to the samples.

Halogen lamps, in particular metal-halogen lamps, fluorescent lamps or UV light-emitting diodes may also be used as UV radiation sources, instead of xenon lamps.

A holding plate 5, which is mounted in the weathering chamber 1, is located opposite the UV radiation sources 2 in order to accommodate and hold material samples 6 to be weathered and temperature sensors such as a blackboard or black standard sensor 7. The beam path of the radiation emitted from the UV radiation sources 2 is illustrated by means of arrows. This results in a three-dimensionally virtually constant radiation power on the plane of the material samples 5.

Sensors 3 and 4 are provided for the measurement of the UV radiation power, and are inserted into openings in a wall of the weathering chamber 1, with this wall being located at right angles to that wall of the weathering chamber 1 to which the UV radiation sources 2 are fitted. The sensors 3 and 4 are thus inclined at an angle to the UV radiation sources 2.

In the present exemplary embodiment, the weathering apparatus has three UV radiation sources 2. Each of the three UV radiation sources 2 has a respectively associated broadband UV sensor 3, which has a sensitivity range from 300 nm to 400 nm and whose output signal is thus a measure of the radiation power emitted by the respectively associated UV radiation source 2 in this spectral range.

Figure 2:
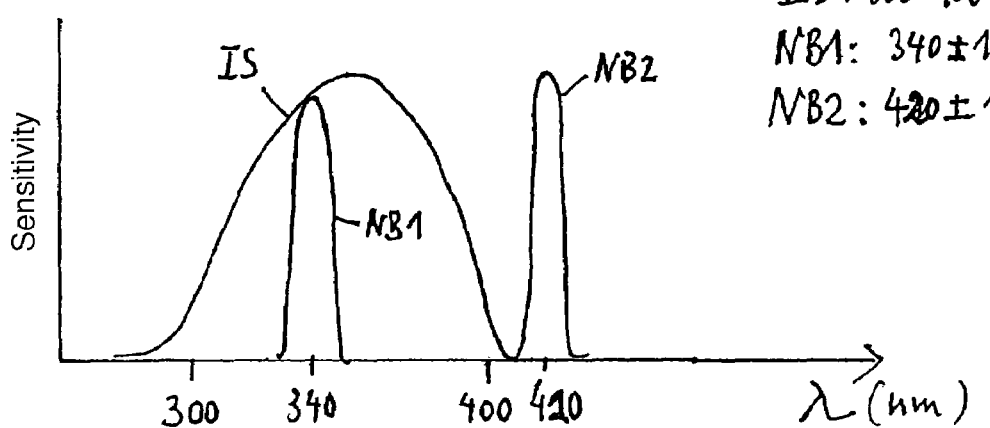
FIG. 2 shows the spectral position of the three measurement ranges specified in the IS and NB Standards.

The weathering apparatus can thus carry out weathering processes with the UV radiation power being measured progressively using the IS Standard, that is to say for the UV bandwidth from 300 nm to 400 nm. However, according to the invention, the weathering apparatus is intended to be able to additionally record the weathering process for measurement purposes using different radiation power data in other bandwidths. For this purpose, one of the UV sensors 3 is calibrated not only for the range from 300 nm to 400 nm but additionally for the spectral range from 330 nm to 350 nm, which is within this spectral range. In FIG. 2, the sensitivity range of the UV sensors 3 and the spectral range of 340 nm ±10 nm, which is contained in this range, are represented by the curves IS and NB1. By way of example, the relevant UV sensor 3 will have been calibrated in advance by means of a UV radiation source and a narrowband UV sensor for the range from 330 nm to 350 nm, in such a way that a conversion factor for the radiation power in the narrowband range is determined from its output signal for the broadband range. This conversion factor may turn out to be a constant parameter from this calibration; however, it is also possible for the conversion factor to be a variable parameter, so that a different conversion factor must be used for calculation of the radiation power in the narrowband range for each output signal from the UV sensor 3 for the broadband range.

The relevant UV sensor 3 may in this case likewise be calibrated by means of one of the UV radiation sources 2 within the weathering chamber 1 in the weathering apparatus, in which case the UV sensor 3 and a narrowband UV sensor for the range from 330 nm to 350 nm are subjected to the UV radiation from one of the UV radiation sources, and the output signals from the UV sensors are compared with one another, while the radiation power from the UV radiation source is being varied, with the conversion factor being determined in this way.

This calibration, which is carried out in advance using one of the UV sensors 3, in the range 340 nm ±10 nm can then also be used for the other UV sensors 3 during a weathering process, with their output signal for the broadband range being converted by means of the conversion factor to a radiation power in the narrowband range. The three existing UV sensors 3 can thus be used to carry out a weathering process, with the UV radiation power of the three UV sensors 3 in this case being recorded in the broadband range or in the narrowband range.

Additionally or as an alternative to this, it is possible to provide the capability to record the UV radiation power in a narrowband range at 420 nm ±10 nm according to the NB Standard. This range is outside the UV, and the broadband sensitivity range from 300 nm to 400 nm of the UV sensors 3, as can be seen from the curve NB2 in FIG. 2. An additional sensor 4, which has a sensitivity range from 410 nm to 430 nm, is thus arranged within the weathering chamber 1 and is positioned in such a way that it records only the radiation from one specific UV radiation source 2. As illustrated, it can be placed in an opening in the side wall, in such a way that it is positioned above the UV sensor 3 associated with this UV radiation source 2 and, like this, is aligned at an inclined angle with respect to the UV radiation source 2. During a weathering process, these two sensors 3 and 4 thus measure the radiation power emitted from the UV radiation source 2 associated with them in the broadband range and in the narrowband range. This UV radiation source is used, so to speak, as a reference radiation source. Only the broadband UV sensors 3 are associated with the other UV radiation sources 2, so that, initially, they directly measure only the radiation power in the broadband range. However, the broadband radiation power measured by them can be used to deduce the radiation power in the narrowband range by relating the radiation powers $UV_{300-400}$ and $VIS_{420}$ measured by the first sensor 3 and the second sensor 4 of the reference radiation source, and by applying them to the broadband radiation power, in particular multiplying them by this. Within certain tolerances, there is a fixed ratio between $VIS_{420}/UV_{300-400}$. This value determined for the reference radiation source can be multiplied by the $UV_{300-400}$ values of the other radiation sources in order to calculate their $VIS_{420}$ values.

It is thus possible to record the radiation powers of the UV radiation sources 2 by the use of only one additional sensor 4 during a weathering process in accordance with the NB Standard, for the narrowband UV range 420 nm ±10 nm, as well.

Thus, when using both aspects of the invention in the described exemplary embodiment, just four sensors are sufficient instead of nine sensors as in the prior art. In general terms, where 3N sensors are required in the prior art for the N radiation sources, 2N−1 sensors can be saved according to the invention, since only N+1 sensors are required.

The invention claimed is:

1. Weathering apparatus comprising:
   an UV radiation source; and
   a first sensor, which is calibrated for a first spectral sensitivity range in the UV and which produces an output signal representative of the radiation power received in the first sensitivity range, wherein
   the first sensor additionally calibrated in such a way that the radiation power of a second spectral sensitivity range which is located within the first spectral sensitivity range can be determined from said output signal.

2. Weathering apparatus according to claim 1, wherein a second sensor is provided, which is calibrated for a third spectral sensitivity range.

3. Weathering apparatus according to claim 1 or 2, wherein the first sensitivity range extends from 300 nm to 400 nm.

4. Weathering apparatus according to claim 1 or 2, wherein the second spectral sensitivity range extends from 330 nm to 350 nm.

5. Weathering apparatus according to claim 2, wherein the third spectral sensitivity range extends from 410 nm to 430 nm.

6. Weathering apparatus according to claim 1, 2, or 5, wherein at least two UV radiation sources are provided, one of which is in each case associated with one of the first sensors and detects essentially the UV radiation from the respectively associated UV radiation source.

7. Weathering apparatus according to claim 2 or 5, wherein the second sensor is associated with a UV radiation source that is used as a reference radiation source, and detects essentially the radiation from the reference radiation source.

8. Weathering apparatus according to claim 7, wherein the radiation power from a UV radiation source in the third spectral sensitivity range can be derived from the output signal from its associated first sensor and the output signals from the first sensor and from the second sensor for the reference radiation source.

9. Weathering apparatus comprising:
   one or more UV radiation sources; and
   one or more first sensors, which are calibrated for a first spectral sensitivity range in the UV and each produce an output signal which is representative of the radiation power received in the first sensitivity range, wherein
   one of the first sensors is additionally calibrated in such a way that the radiation power of a spectral range which is located within the first spectral sensitivity range can be determined from its output signal;
   wherein the weathering apparatus has a weathering chamber in which the UV radiation sources and the UV sensors are accommodated, the UV radiation sources are arranged along a first wall of the weathering chamber, the samples to be weathered are arranged along a second wall, which is opposite the first wall, and the UV sensors are fitted to a third wall, which connects the first wall and the second wall, and in particular are inserted into openings in the third wall.

10. Weathering apparatus according to claim 9, wherein the samples to be weathered are held by the second wall or by a holding plate.

11. Weathering apparatus according to claim 2, wherein at least two UV radiation sources are provided, one of which is in each case associated with one of the first sensors and detects essentially the UV radiation from the respectively associated UV radiation source.

12. Weathering apparatus according to claim 3 wherein the second sensor is associated with a UV radiation source that is used as a reference radiation source, and detects essentially only the radiation from the reference radiation source.

13. Weathering apparatus comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;
wherein the first sensitivity range extends from 300 nm to 400 nm; and
wherein the weathering apparatus has a weathering chamber in which the UV radiation sources and the UV sensors are accommodated,
the UV radiation sources are arranged along a first wall of the weathering chamber,
the samples to be weathered are arranged along a second wall, which is opposite the first wall, and
the UV sensors are fitted to a third wall, which connects the first wall and the second wall, and in particular are inserted into openings in the third wall.

14. Weathering apparatus according to claim 7, comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;
wherein a second sensor is provided, which is calibrated for a second spectral sensitivity range;
wherein the second sensor is associated with a UV radiation source that is used as a reference radiation source, and detects essentially only the radiation from the reference radiation source; and
wherein the weathering apparatus has a weathering chamber in which the UV radiation sources and the UV sensors are accommodated,
the UV radiation sources are arranged along a first wall of the weathering chamber, the samples to be weathered are arranged along a second wall, which is opposite the first wall, and
the UV sensors are fitted to a third wall, which connects the first wall and the second wall, and in particular are inserted into openings in the third wall.

15. Weathering apparatus comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;
wherein a second sensor is provided, which is calibrated for a second spectral sensitivity range; and
wherein the weathering apparatus has a weathering chamber in which the UV radiation sources and the UV sensors are accommodated, the UV radiation sources are arranged along a first wall of the weathering chamber, the samples to be weathered are arranged along a second wall, which is opposite the first wall, and the UV sensors are fitted to a third wall, which connects the first wall and the second wall, and in particular are inserted into openings in the third wall.

16. Weathering apparatus comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;
wherein a second sensor is provided, which is calibrated for a second spectral sensitivity range;
wherein the second spectral sensitivity range extends from 410 nm to 430 nm; and
wherein the weathering apparatus has a weathering chamber in which the UV radiation sources and the UV sensors are accommodated, the UV radiation sources are arranged along a first wall of the weathering chamber, the samples to be weathered are arranged along a second wall, which is opposite the first wall, and the UV sensors are fitted to a third wall, which connects the first wall and the second wall, and in particular are inserted into openings in the third wall.

17. Weathering apparatus comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;
wherein a second sensor is provided, which is calibrated for a second spectral sensitivity range;
wherein the first sensitivity range extends from 300 nm to 400 nm; and
wherein the weathering apparatus has a weathering chamber in which the UV radiation sources and the UV sensors are accommodated, the UV radiation sources are arranged along a first wall of the weathering chamber,
the samples to be weathered are arranged along a second wall, which is opposite the first wall, and
the UV sensors are fitted to a third wall, which connects the first wall and the second wall, and in particular are inserted into openings in the third wall.

18. Weathering apparatus comprising:
one or more UV radiation sources; and
one or more first sensors, which are calibrated for a first spectral sensitivity range in the UV and each produce an output signal which is representative of the radiation power received in the first sensitivity range, wherein
one of the first sensors is additionally calibrated in such a way that the radiation power of a spectral range which is located within the first spectral sensitivity range can be determined from its output signal;

wherein a second sensor is provided, which is calibrated for a second spectral sensitivity range;

wherein the second spectral sensitivity range extends from 410 nm to 430 nm;

wherein the second sensor is associated with a UV radiation source that is used as a reference radiation source, and detects essentially only the radiation from the reference radiation source; and wherein the weathering apparatus has a weathering chamber in which the UV radiation sources and the UV sensors are accommodated, the UV radiation sources are arranged along a first wall of the weathering chamber, the samples to be weathered are arranged along a second wall, which is opposite the first wall, and the UV sensors are fitted to a third wall, which connects the first wall and the second wall, and in particular are inserted into openings in the third wall.

* * * * *